United States Patent [19]
Lavin

[11] Patent Number: 5,114,023
[45] Date of Patent: May 19, 1992

[54] UTILITY TRAY FOR INTRAVENOUS POLE

[76] Inventor: Janice A. Lavin, 242 Lake Shore Dr., Crystal Lake, Ill. 60014

[21] Appl. No.: 646,241

[22] Filed: Jan. 28, 1991

[51] Int. Cl.$^5$ .............................................. A47F 5/08
[52] U.S. Cl. .................................. 211/107; 248/125; D24/128
[58] Field of Search ................... 211/107, 110, 72, 78, 211/205; 248/125, 132; 604/250, 256; D24/128

[56] References Cited

U.S. PATENT DOCUMENTS

| | | | |
|---|---|---|---|
| D. 281,453 | 11/1985 | Digianfilippo et al. | D24/128 |
| D. 298,355 | 11/1988 | Young | D24/128 |
| D. 310,570 | 9/1990 | Wells | D24/128 |
| 2,954,028 | 9/1960 | Smith | 604/250 X |
| 3,338,628 | 8/1967 | Evans | 211/72 X |
| 3,414,133 | 12/1968 | Guerri et al. | 248/132 |
| 3,746,601 | 7/1973 | Strony | 211/205 X |
| 4,533,347 | 8/1985 | Deckert | 604/250 X |

Primary Examiner—Blair M. Johnson
Assistant Examiner—Korie Chan
Attorney, Agent, or Firm—Alan B. Samlan

[57] ABSTRACT

A utility tray for supporting medical paraphernalia and guiding hollow tubing which is adapted for mounting to an upstanding vertical pole used for supporting intravenous solution containers. The tray has a plurality of varying diameter circular openings for receiving and supporting cylindrical objects. A clamp along one edge of the tray is used to attach the tray to the upstanding vertical pole. Slots cut along an edge of the tray have a gradually diminishing width to receive hollow tubing. By pushing the tubing into the slot, the flow of fluids through the tubing is stopped. Tube guides also cut along the perimeter edge of the tray are used to keep several tubes from becoming intertwined.

15 Claims, 2 Drawing Sheets

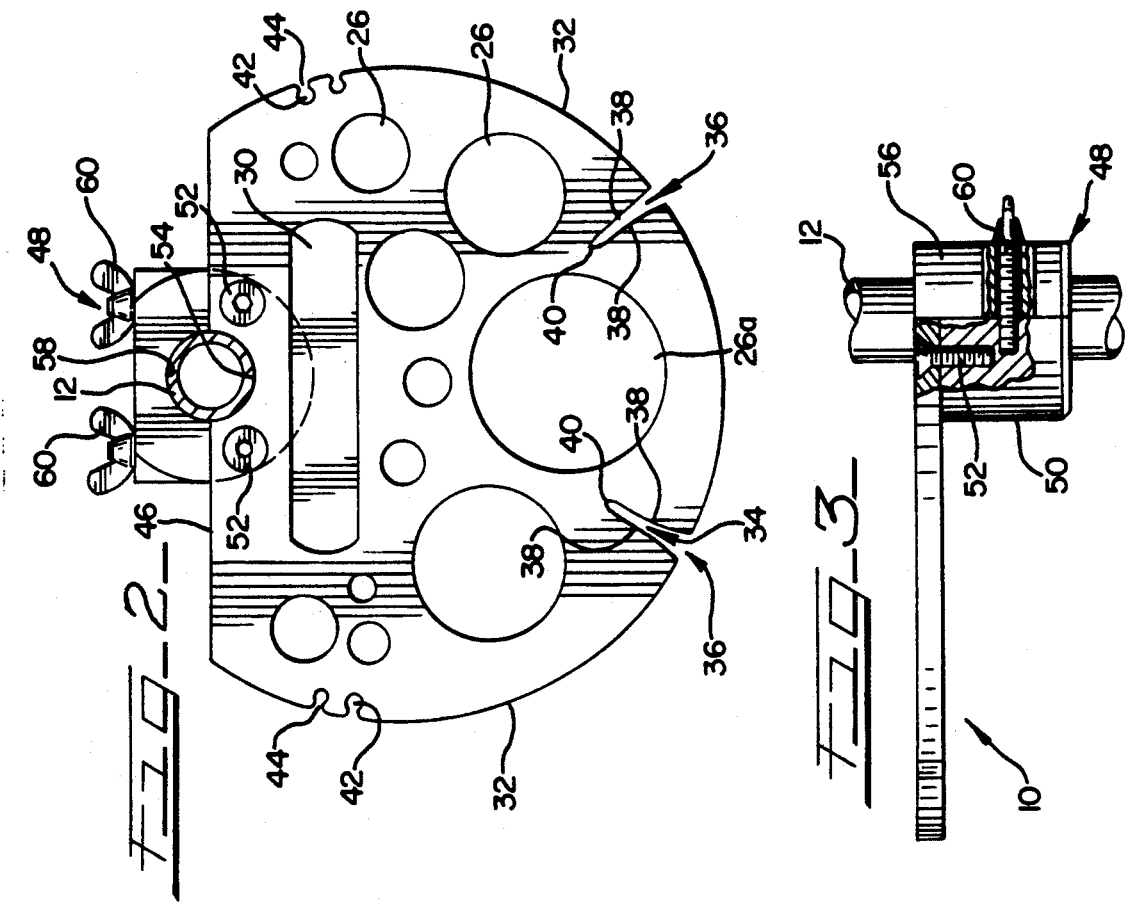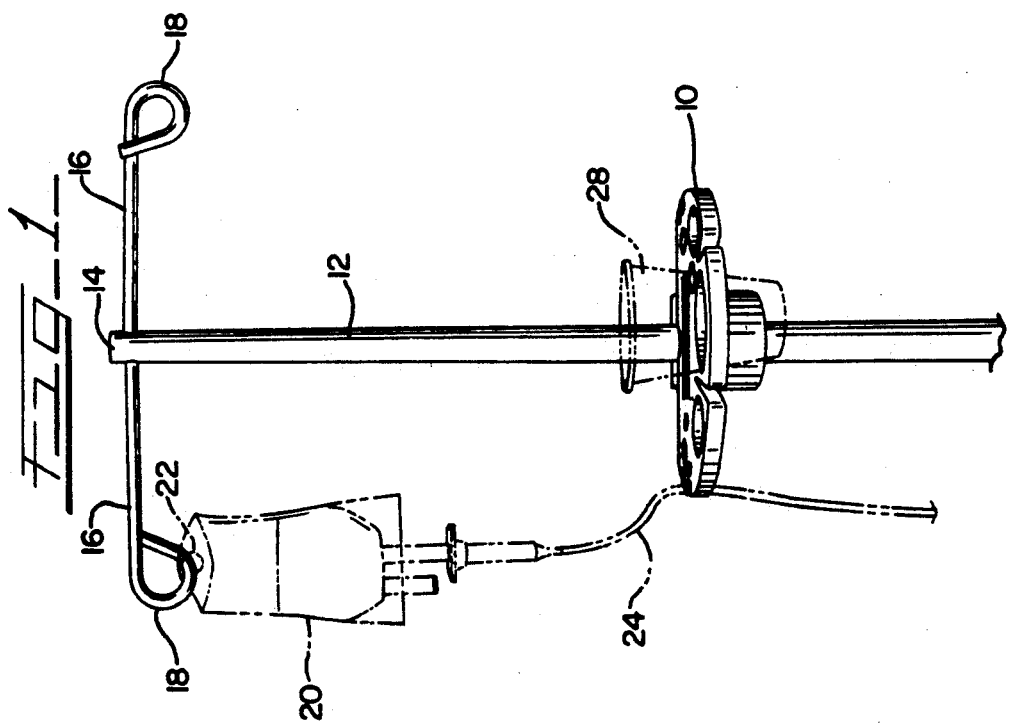

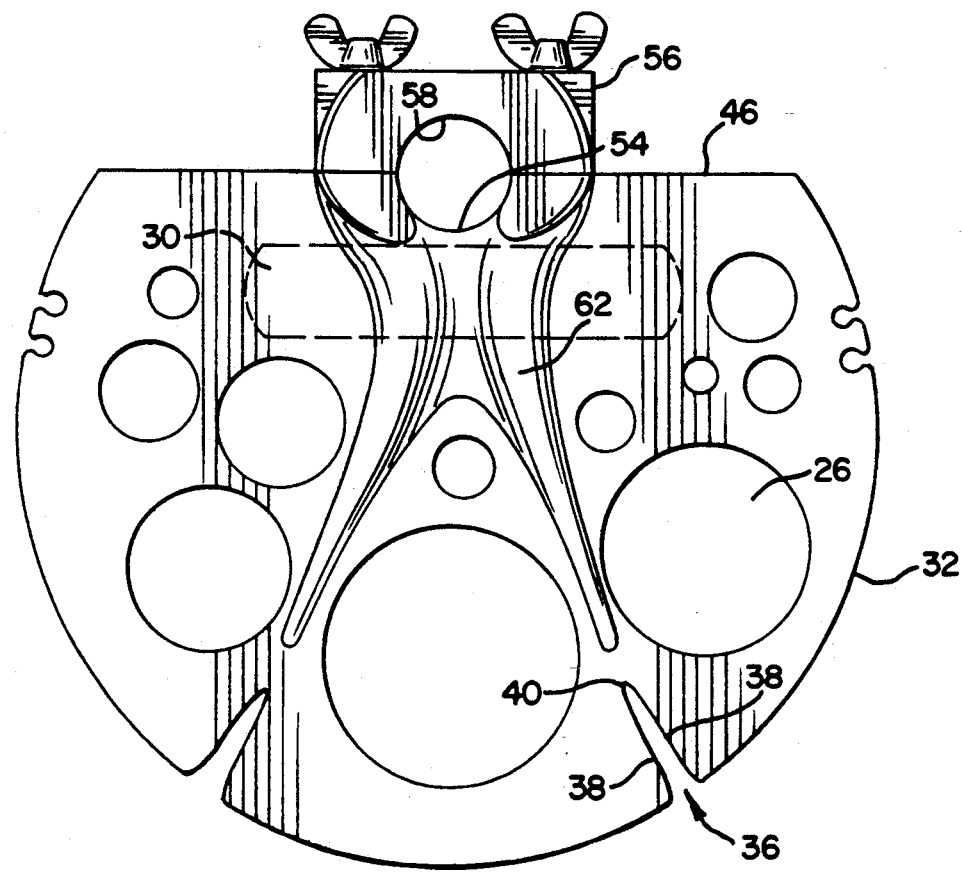
FIG_4_
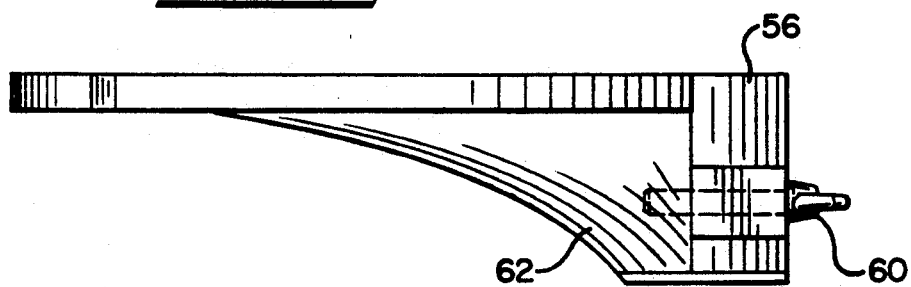
FIG_5_

5,114,023

UTILITY TRAY FOR INTRAVENOUS POLE

BACKGROUND AND SUMMARY OF THE INVENTION

This invention relates to a utility tray which is mounted to an upstanding vertical pole used for supporting intravenous solution containers. The purpose of the tray is for the convenience of the medical staff by holding various items needed during the tube feeding or intravenous infusion process.

It is common for patients in hospitals and nursing homes to require intravenous tubes for food or medication. The intravenous solution containers are supported above the feeding point by a vertical upstanding pole having container hangers at the top and wheels at the bottom. The term intravenous pole used herein refers to the vertical upstanding pole in this intravenous setting.

Nurses in nursing homes who must administer tube feedings find it difficult to flush the tubing, add more formula, or change the medication when the resident is out in the hall or has been placed in an activities room for diversion. Although these residents have a large syringe issued to them for the purpose of irrigating or flushing, it is usually kept in the resident's bureau of their bedroom. It would be a great convenience and save much nursing time if the syringe is with the patient. Furthermore, the syringe may be needed in an emergency. However, as no syringe should be stored on a tray or in close proximity to a patient with a needle intact, the inventive device should only be used in conjunction with a catheter tipped syringe which does not require a needle.

In a hospital setting, a tray is necessary to hold the same items in order to save nursing time and physical energy. The items necessary for the medical staff to do their routine work will be readily available while items required for possible emergencies will also be on hand conserving time in a life threatening situation.

Also, as the patient is ambulatory, he is able to be up and out of bed and may be walking in the hallway or going to other parts of the hospital. With one hand holding the intravenous pole and guiding it as he is walking, there is little ability to carry the other necessary items required by the patient for his hygiene. Thus, from a patient's perspective it would be convenient to be able to carry toiletries such as a toothbrush, toothpaste, comb, brush, water glass, etc. as he walks through the hospital. The freedom of the patient's hands during these walks would give him a safer environment in which to ambulate by having both hands free, thus reducing the possibility of accidents.

In the past, there have been various types of attachments adapted to be fitted to variously configured vertically upstanding poles. One example is illustrated in U.S. Pat. No. 1,799,079 entitled "Washstand". In this patent the wash basin is attached by means of a sleeve which encircles the upstanding tubular pole However, this device is not easily removed from the pole nor is it adapted for receiving and retaining various medical paraphernalia, which would be found in a medical environment.

U.S. Pat. No. 3,414,133 entitled "Small Hanging Basket for Beach Umbrellas" illustrates a hanging basket which is used for beach umbrellas. A major problem with the several embodiments illustrated in this patent is that none of them are easily attached to or can be removed from the umbrella pole. Also, the basket does not have holes formed in the basket to receive glasses, syringes, etc. Rather, a separate shelf is added to the basket which can be used to receive bottles, etc. U.S. Pat. No. 4,678,089 entitled "Display Stand" illustrates a display device having a series of trays mounted on a pole. These trays do not have holes or other receiving means thereof to receive cups, syringes or other medical paraphernalia. Furthermore, the trays are not easily removable from the vertically upstanding pole.

U.S. Pat. No. 3,194,403 entitled "Holder on Upright Support of Detachable Rotatable Trays" illustrates the use of a mounting plate which is mounted on the vertically upstanding pole. Variously configured holders or rings are then affixed to the mounting plate. Although the holders or rings can be removed, the mounting plate is designed to remain on the pole and can only be removed from the pole by being slid over one of the ends of the pole. If both ends of the vertically upstanding pole have extensions or protrusions, such as in the case of an intravenous pole, the plate could not be removed.

As can be seen from the prior art described above, there is a common problem which has not been solved by these prior art devices. The intravenous pole which is used in a medical environment to support intravenous containers is generally configured such that it has its lower end attached to a transport mechanism, such as a wheel or caster arrangement, and its top end has support arms extending outward which are used to support the intravenous containers. Accordingly, any sort of device to be mounted on the pole could not be slid over the top of the pole or up from the bottom of the pole as both ends of the pole have restrictions which preclude any sort of mounting device from being slid over the pole from either end. Therefore, any sort of attachment to the pole must necessarily have a mounting arrangement configured such that it can be affixed to the mid section of the pole without the necessity of sliding it over either end.

Furthermore, the needs of the medical staff are specific. The applicant's medical tray is designed for holding various items needed during the tube feeding or intravenous infusion process. The items which must be held may include syringes used for irrigating tubes, adding fluids, medications, or feeding. Airways are often needed near the bedside for emergency precautions or during cardiac arrest. Hemostats and clamps are often kept near the patient to clamp off a tube in case of complications. Bandages and scissors may need to stay at the bedside for non-sterile functions. Plastic medicine cups to hold petroleum jelly, peroxide, corn starch and other miscellaneous items are often required at the bedside. A water cup for drinking, flushing or rinsing of tubes is also convenient. Sterile dressings in their unopened packages and tape for securing intravenous catheters is also kept at the bedside. Other items which would be conveniently retained at the bedside include cotton balls and a container, gloves, tongue blades, stickers for affixing to an intravenous solution bag to identify the medications, alcohol preparation pads, pins, markers, and miscellaneous paraphernalia related to the patient's condition.

Applicant's invention is designed to be used with an upstanding vertical pole used to support intravenous solution containers. At the bottom of the pole are rollers for permitting the pole to be easily transportable by rolling it along the floor. The utility tray has a clamp along one of the perimeter edges to attach the tray to an intermediate portion of the vertical pole without the necessity of sliding it over the top or up from the bottom of the pole. There are a series of circular openings in the utility tray for receiving in a supporting mode various sized cylindrical objects. There is also a recessed trough portion on the surface of the utility tray for receiving and supporting miscellaneous medical items. A u-shaped slot is cut into the perimeter edge of the tray with the width of the slot gradually diminishing from the edge of the tray towards the base of the slot. The slot is used for receiving hollow tubes of various diameter and to pinch the tube closed as it is moved from the open end towards the base of the slot to stop the flow of fluid through the tube. In addition there are circular areas cut into the top of the tray to permit tubes to be held in the circular areas thereby restraining axial movement of the tubes in an effort to keep the tubes from being tangled with one another.

OBJECTS AND ADVANTAGES

Accordingly, it is an object of the present invention to supply a tray which can be easily fastened to the intravenous pole. Related to this object is the object of providing a tray which can be mounted to the pole without the necessity of sliding it over the top or up from the bottom of the pole, which is impossible with a pole used to support intravenous solutions.

Another object is the object of providing a tray which can support various medical apparatus by means of holes which will receive the apparatus in a supporting relationship. Another object is the object of providing a tray having a recessed portion to support and retain other medical paraphernalia.

Yet another object is to provide a tray having a slot cut in its edge, with the width of the slot gradually diminishing towards the base of the slot such that the slot can receive hollow tubes of various diameters, which can be pinched closed as they are moved towards the base of the slot to stop the flow of fluid through the tube. An advantage of such a slot is that it permits the medical practitioner to selectively stop the flow of fluid through the tube as required for the patient's care, while leaving the practitioner's hands free to treat the patient.

Yet another object is the object of providing a tray having circular cut out portions to hold and restrain from axial movement various tubes. The advantage is that this will keep the tubes from becoming entangled with each other.

Still another object is the object of providing a utility tray which may be either manufactured of metal and can be easily sterilized, or can be manufactured of an inexpensive plastic and thus be a disposable item. Related to this object is the object of providing a mounting bracket attached to the pole such that the tray can be easily attached to the mounting bracket or removed therefrom for disposal. These and other objects and advantages will become apparent upon reading the brief description of the drawings and detailed description of the preferred embodiments.

BRIEF DESCRIPTION OF THE DRAWINGS

FIG. 1 is a perspective view of the utility tray mounted to a vertical upstanding pole used to support intravenous solution containers with portions of the vertical pole removed.

FIG. 2 is a plan view of the utility tray mounted on the intravenous pole.

FIG. 3 is a side view partially in cross section with portions removed of the utility tray mounted on the intravenous pole.

FIG. 4 is a bottom view of an alternate embodiment of the utility tray which has a support bracket molded as a part of the utility tray to give additional strength to the tray.

FIG. 5 is a side view of the utility tray illustrated in FIG. 4.

DESCRIPTION OF THE PREFERRED EMBODIMENT

Turning first to FIG. 1 there is illustrated a utility tray 10 of the present invention. It is mounted on the mid section of a vertical upstanding intravenous pole 12 used to support intravenous solution containers. The vertical pole 12 has a top end 14 from which extends a pair of horizontal support arms 16 terminating in hooked ends 18. An intravenous solution container or bag 20 has a circular opening 22 which extends over the hooked end 18 and is supported thereby. An intravenous feeding tube 24 exits from the bottom of the solution bag 20 and is connected thereto in the conventional manner.

In FIG. 2, which is a top view of the tray, the various configured cut outs and recessed portions are illustrated. There are a plurality of circular openings 26 of varying diameters. One such opening 26a is of the proper size to accept and retain in a supporting relationship a water glass 28. The other openings 26 are of varying diameters to receive and support syringes, pill containers, clamps, scissors, etc. A recessed trough 30 which has a length, a width and a depth which does not pass through the bottom side of the tray 10 is used to receive and hold labels, clips, bandages, and other small medical devices. The tray 10 has a perimeter edge 32 which has a pair of slots 34 cut therein. A slot is defined by an open end 36 at the perimeter edge 32, and a pair of tapering walls 38 which terminate in a bottom u-shaped wall 40. The purpose of the gradually tapering walls 38 is to receive hollow tubing such as the intravenous tube 24, which has fluids flowing through it. If the doctor or nurse desires to cut off the flow of fluid through the tube 24, they can merely place it within the slot 34 and push it towards the bottom u-shaped wall 40. The tapering walls 38 will pinch the tube closed cutting off the flow of fluid through it. This leaves the doctor's or nurse's hands free for other tasks.

Also seen in FIG. 2 are a plurality of tube guides 42 placed adjacent to the perimeter edge 32. Opening passageways 44 connect the tube guides with the perimeter edge 32 whereby the intravenous tube 24 can be pushed through the opening passageway 44 and retained within the tube guides 42. This keeps the intravenous tubes 24 from being tangled with each other or with any of the other medical paraphernalia on the tray. The dimensions of the tube guides 42 and opening passageway 44 can vary depending upon the diameter of the intravenous tubes 24 which they are to receive and retain.

Along a back wall 46 of the tray 10 are clamping means 48, which firmly attach the utility tray 10 to the upstanding intravenous pole 12. As seen in FIG. 3, there is a front half of the clamp 50 attached to the underside of the tray 10 by mean of screws 52. Alternatively, the front half of the clamp 50 can be manufactured integrally with the utility tray 10 as a unitary piece. The front half of the clamp 50 has a semi-cylindrical cut out 54 in the back wall 46. The diameter of the semi-cylindrical cut out 54 is designed to be the same as the outer diameter of the intravenous pole 12. There is a rear half of a clamp 56 which also has a cylindrical cut out 58 which should be of the same diameter as the vertical pole 12. Two screws 60 pass through the rear half of the clamp 56 and into the front half of the clamp 50. The screws 60 firmly clamp the rear half of the clamp 56 to the front half of the clamp 50 thereby capturing in a locking engagement the vertical pole 12 between the two clamp portions.

In the embodiment illustrated in FIGS. 1 through 3, the utility tray 10 is manufactured from heavy plastic which can be injection molded or can be made from a metal such as aluminum or stainless steel. In this embodiment the tray 10 is designed to be reusable if it is sterilized after each use. However, the device can be made of a disposable material such as a thin gauge plastic, which is designed to be used by one patient and then discarded. Such a disposable tray is illustrated in FIGS. 4 and 5.

The tray 10 as seen in FIG. 4 is substantially similar to the device illustrated in FIGS. 1 through 3. However, the tray is manufactured of a thin plastic or thermoplastic material having a support bracket 62 molded as a part of the tray 10. The reason the tray requires such a support bracket is that it is manufactured from a very thin sheet of plastic, which may lack sufficient structural strength without the bracket. The tray 10 may be vacuum or injection formed. The rear half of the clamp 56 is made as a separate block and will clamp around the vertical pole 12 just a the embodiment illustrated in FIG. 3. However, the screws 60 will pass through a passageway in the rear half of the clamp 56 and screw into the support bracket 62. The semi-cylindrical cut outs 54 and 56 are the same as in the previous embodiment and the diameter of the cut out area is substantially identical to the diameter of the vertical pole 12.

In another alternative embodiment the clamping means can be a flexible strap having its opposite ends fastened to a block on the tray adjacent to the back wall 46. The strap passes around the upstanding vertical intravenous pole 12. As the strap is tightened, it clamps around the pole 12 with sufficient strength to support the tray 10.

In another alternative embodiment, the mounting bracket may be permanently or semi-permanently affixed to the vertical upstanding pole 12 and the tray 10 can be attached to the permanent or semi-permanent mounting bracket. The various methods of attaching the tray to the mounting bracket are numerous and can include threaded fasteners, pins and pin receiving holes, tabs and slots, etc.

Thus, there is provided a utility tray adapted for mounting on a pole used to support intravenous feeding solution containers that fully satisfies the aims, objects and advantages set forth above. It is evident that many alternatives, modifications and variations will be apparent to those skilled in the art. Accordingly, it is intended to embrace such variations as fall within the spirit and broad scope of the appended claims.

What is claimed is:

1. A tray and pole combination comprising:
   an upstanding vertical pole having top and bottom ends;
   roller means attached to the bottom end of the vertical pole for permitting the pole to be easily transportable by rolling along a floor surface;
   support arms extending outward from the top end of the vertical pole, the support arms having means for hanging intravenous solution containers;
   a utility tray having a planar top surface and perimeter edges;
   clamping means disposed along the perimeter edge for attaching the utility tray to an intermediate portion of the vertical pole;
   a plurality of varying diameter circular openings in the utility tray for receiving in a supporting relationship cylindrical objects;
   a recessed trough portion on the planar top surface of the utility tray for receiving and supporting miscellaneous objects of varying sizes; and
   a slot disposed along the perimeter edge, the slot being open at the perimeter edge, the width of the slot gradually diminishing from the open perimeter edge to the base of the slot, the slot adapted for receiving hollow tubes of various diameters and to pinch the tube closed as the tube is moved from the open end towards the base of the slot to stop the flow of fluid through the tube.

2. The combination of claim 1 and further comprising a tube guide having a substantially circular area cut into the utility tray with an opening passageway extending from the perimeter edge to the circular area to permit the tube to pass through the opening passageway and into the circular area where the tube is restrained from axial movement.

3. The combination of claim 1 wherein the clamping means comprises a semi-cylindrical area in the perimeter edge dimensioned to receive one-half of the circumference of the vertical pole and a semi-cylindrical clamp adapted to receive the other half of the circumference of the vertical pole, the clamp having fastening means to be secured to the utility tray to securely lock the utility tray to the pole.

4. The combination of claim 2 wherein at least one of the circular openings is dimensioned to receive a water glass and at least one of the circular openings is dimensioned to receive a syringe.

5. The combination of claim 1 wherein the clamping means comprises a locking band that encircles a portion of the vertical pole, the band attached to the tray, and means for tightening the band around the pole to secure the tray to the pole.

6. A utility tray for supporting medical paraphernalia and guiding hollow tubing, the tray adapted for mounting to an upstanding vertical pole used for supporting intravenous solution containers, the tray comprising:
   a planar top surface and perimeter edges;
   fastening means disposed along the perimeter edge of the tray for attaching the tray to an intermediate portion of the vertical pole;
   a plurality of varying diameter circular openings in the utility tray for receiving and supporting cylindrical objects;
   a recessed trough portion with a closed bottom on the planar surface of the tray for receiving and supporting objects of varying sizes which fit into or supported by the recessed trough;
   a slot disposed along the perimeter edge, the slot having an opening at the perimeter edge and extending into a base thereof disposed in the body of the tray, the slot having a width defined by walls extending from the opening to the base, the width of the slot gradually diminishing from the opening to the base, the slot adapted for receiving hollow tubes of various diameters and to pinch the tube closed as the tube is moved from the opening towards the base of the slot to stop the flow of fluid through the hollow tube; and a tube guide having a substantially circular area disposed adjacent the perimeter edge of the tray to receive and releasably retain the hollow tubing.

7. The tray of claim 6 wherein the tube guide has an opening passageway extending from the perimeter edge to the circular area to permit the hollow tubing to pass through the opening passageway and into the circular area where the tubing is restrained from axial movement.

8. The tray of claim 6 wherein the fastening means comprises a semi-cylindrical area in the perimeter edge adapted to receive one-half of the circumference of the vertical pole and a semi-cylindrical clamp adapted to receive the other half of the circumference of the vertical pole, the clamp having fasteners to secure the clamp to the tray with the pole securely held between the clamp and the tray.

9. The tray of claim 7 wherein at least one of the circular openings is dimensioned to receive a water glass and at least one of the circular openings is dimensional to receive a syringe.

10. The tray of claim 6 wherein the fastening means comprises a locking band that encircles a portion of the vertical pole, the band attached to the tray, and means for tightening the band around the pole to secure the tray to the pole.

11. The utility tray of claim 6 wherein the fastening means for attaching the tray to the vertical pole comprises a clamping piece for encircling the intermediate portion of the vertical pole, the clamping piece having means to tighten the clamping piece to the pole to securely mount the clamping piece to the pole, receiving means on the clamping piece to receive in a supporting and locking relationship the utility tray, whereby the utility tray can be readily removed from the clamping piece.

12. The utility tray of claim 11 wherein the clamping piece has a groove cut therein which is received by a complimentary tab on the utility tray.

13. A tray and pole combination comprising:
an upstanding vertical pole having top and bottom ends;
roller means attached to the bottom end of the vertical pole for permitting the pole to be easily transportable by rolling along a floor surface;
support arms extending outward from the top end of the vertical pole, the support arms having means for hanging intravenous solution containers;
a utility tray having a planar top surface and perimeter edges;
fastening means disposed along the perimeter edge for attaching the utility tray to an intermediate portion of the vertical pole;
a plurality of varying diameter circular openings in the utility tray for receiving in a supporting relationship cylindrical objects;
a recessed trough portion on the planar top surface of the utility tray for receiving and supporting miscellaneous objects of varying sizes; and
a slot disposed along the perimeter edge, the slot being open at the perimeter edge, the width of the slot gradually diminishing from the open perimeter edge to the base of the slot, the slot adapted for receiving hollow tubes of various diameters and to pinch the tube closed as the tube is moved from the open end towards the base of the slot to stop the flow of fluid through the tube.

14. The combination of claim 13 wherein the fastening means for attaching the tray to the vertical pole comprises a clamping piece for encircling the intermediate portion of the vertical pole, the clamping piece having means to tighten the clamping piece to the pole to securely mount the clamping piece to the pole, receiving means on the clamping piece to receive in a supporting and locking relationship the utility tray, whereby the utility tray can be readily removed from the clamping piece.

15. The combination of claim 14 wherein the clamping piece has a groove cut therein which is received by a complimentary tab on the utility tray.

* * * * *